United States Patent [19]

Okudaira et al.

[11] Patent Number: 5,854,276

[45] Date of Patent: Dec. 29, 1998

[54] SUBSTANCE WF16616, PROCESS FOR PRODUCTION THEREOF, AND USE THEREOF

[75] Inventors: Terumi Okudaira, Chiyokawa-mura; Yasuhisa Tsurumi, Tsukuba; Hiroshi Hatanaka, Moriya-machi; Toru Kino, Tsuchiura; Seiji Hashimoto, Tsukuba, all of Japan

[73] Assignee: Fujisawa Pharmaceutical Co., Ltd., Osaka, Japan

[21] Appl. No.: 973,716

[22] PCT Filed: Jun. 21, 1996

[86] PCT No.: PCT/JP96/01725

§ 371 Date: Jan. 26, 1998

§ 102(e) Date: Jan. 26, 1998

[87] PCT Pub. No.: WO97/01575

PCT Pub. Date: Jan. 16, 1997

[30] Foreign Application Priority Data

Jun. 29, 1995 [JP] Japan .................................. 7-185007

[51] Int. Cl.$^6$ ........................ A01N 43/36; C12P 17/16; C07D 209/82; C07D 209/94
[52] U.S. Cl. ...................... 514/424; 435/118; 548/437; 548/450; 548/449
[58] Field of Search ...................... 548/437, 449, 548/450; 435/118

[56] References Cited

FOREIGN PATENT DOCUMENTS 0 311 193  4/1989  European Pat. Off. .
0 486 011  5/1992  European Pat. Off. .
0 644 199  3/1995  European Pat. Off. .

OTHER PUBLICATIONS

Agathos, S.N., Enhancement of Cyclosporin Production in a Tolypocladium Inflatum Strain After Epichlorohydrin Treatment, Journal of Biotechnology, 13 73–78, Dec. 1990.

*Primary Examiner*—Johann Richter
*Assistant Examiner*—Dominic Keating
*Attorney, Agent, or Firm*—Oblon, Spivak, McClelland, Maier & Neustadt, P.C.

[57] ABSTRACT

1. WF16616 substance represented by the following structural formula (1) or its pharmaceutically acceptable salt.

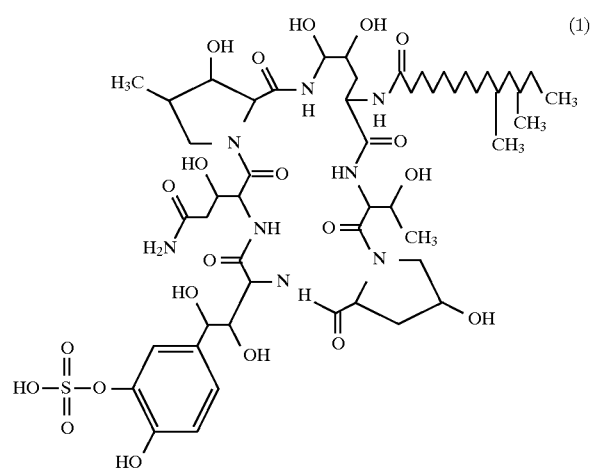

WF16616 substance exhibits an antimicrobial activity, especially an excellent antifungal activity.

5 Claims, 2 Drawing Sheets

SUBSTANCE WF16616, PROCESS FOR PRODUCTION THEREOF, AND USE THEREOF

FIELD OF THE INVENTION

The present invention relates to WF16616 substance, a process for producing the same and use thereof. WF16616 substance is a novel substance which is isolated from a culture broth of microorganisms, especially imperfect fungi. This substance exhibits an excellent physiological activity, and is effective as an antimicrobial agent for humans and other animals, especially as an agent for preventing or treating diseases caused by microorganisms, molds, other fungi or protozoans, such as an antifungal agent and an agent for Pneumocystis carinii pneumonia.

PRIOR ART

A variety of antimicrobial substances have been developed so far, but few of them are satisfactory with respect to effectiveness, antimicrobial spectrum, safety, production cost and the like. Therefore, the development of novel substances has been in high demand in the art.

Problems to be Solved by the Invention

The present invention has been conducted to meet such a demand in the art and to develop a novel substance that exhibits an outstanding physiological activity.

Means Taken for Solving the Problems

The present inventors have conducted various investigations to achieve the above-mentioned purpose. Consequently, they have focussed their attention on fermentative products of microorganisms, and have earnestly screened various microorganisms. As a result, they have newly found that an extract obtained from a culture broth of No. 16616 strain which was newly separated from a soil sample collected in Takato-cho, Nagano-ken exhibits an excellent antimicrobial activity, especially an antifungal activity. They have further studied the physico-chemical properties of this substance in detail, and have identified that this substance is a novel substance which has been so far unknown. They have named this substance "WF16616". Upon further investigations, they have established an industrial process for producing the same, and have completed the present invention.

Figure 1:
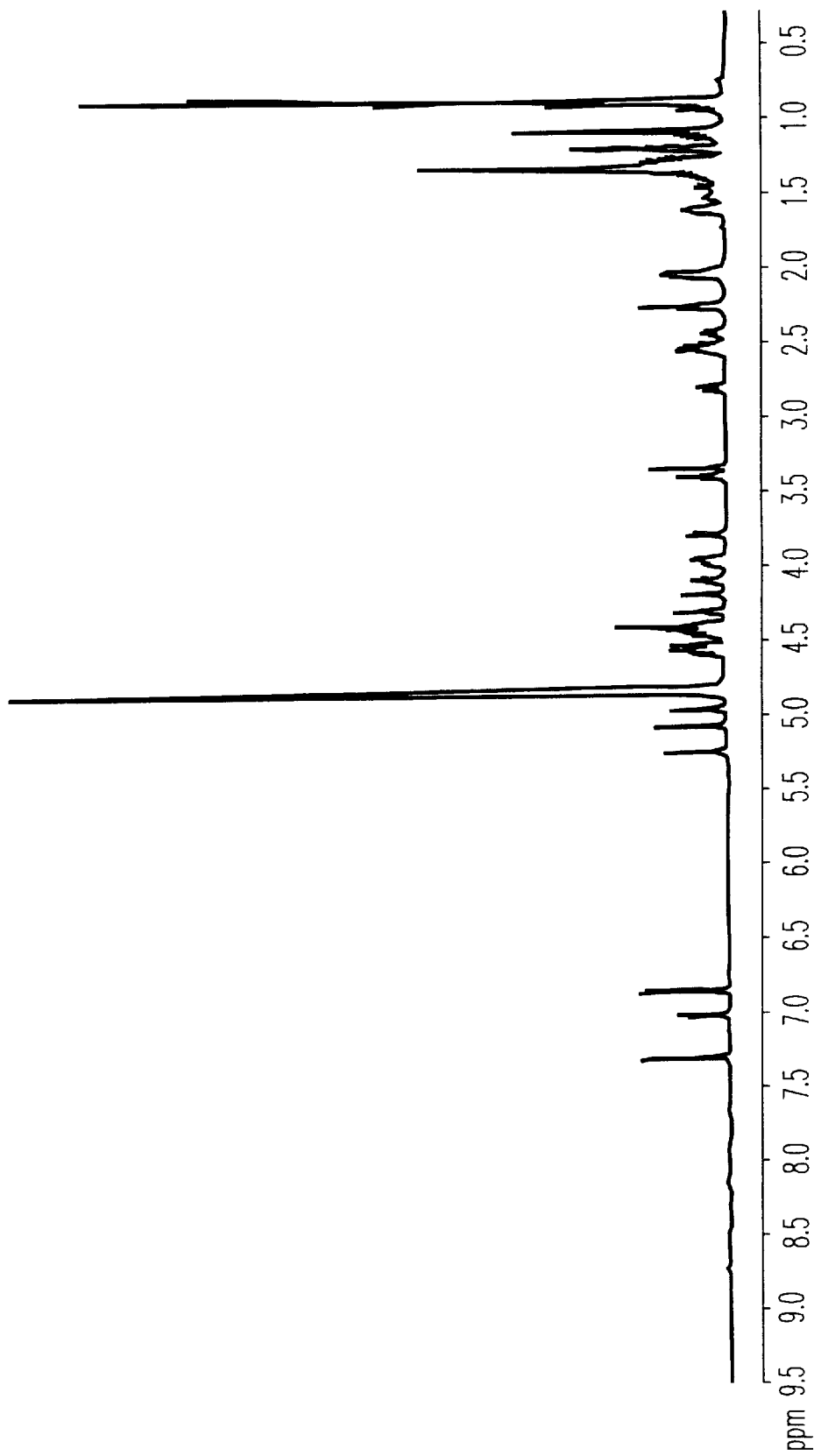
FIG. 1 is a chart showing a $^1$H nuclear magnetic resonance spectrum of a salt (which is considered to be a sodium salt, a potassium salt, an ammonium salt or a mixture thereof) of WF16616 substance.

WF16616 substance of the present invention has been found to be represented by the following structural formula (1) upon studies on physico-chemical properties and the like which will be later described.

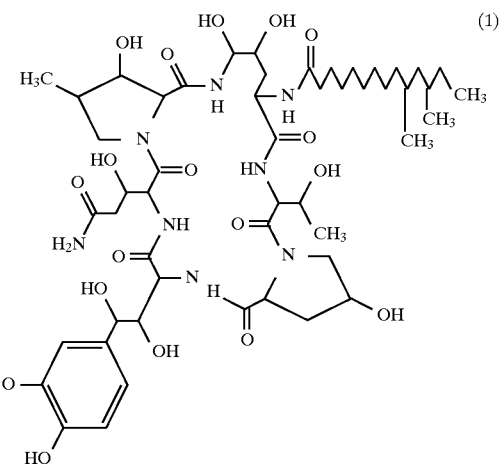

WF16616 substance of the present invention is produced by, for example, No. 16616 strain which is a filamentous fungus separated from a soil sample collected in Takato-cho, Kamiina-gun, Nagano-ken. This microorganism is restrictedly grown on various media and forms a yellowish white colony. Further, on a variety of media No. 16616 strain forms an anamorph consisting of a conidiophore having a verticillate phialide and a sticky conidial mass. The phialide consists of a swollen base and an elongated stem. In view of these morphological characteristics, the microorganism is identied to belong to the genus Tolypocladium W. Gams (Gams, W: Persoonia, 6:185-191, 1971) which is an imperfect fungus. The mycological properties thereof are described below.

The cultural properties of this microorganism in a variety of agar media are summed up in Tables 1 and 2 below. It was restrictedly grown through incubation on a potato dextrose agar medium, and was spread in a diameter of from 1.5 to 2.0 cm after incubation at 25° C. for 2 weeks. The colony surface was felty or cottony, and somewhat raised. The central portion and the peripheral portion of the colony were white to yellowish white, and the portion therebetween was grayish brown. The reverse thereof was olive brown and yellowish white. The conidial structures were abundantly observed. The colony was restrictedly grown on a corn meal agar medium also, and was spread in a diameter of from 1.5 to 2.0 cm under the same conditions. The colony surface was flat, thin and felty. The central portion of the colony was olive gray, and the peripheral portion was yellowish white. The reverse thereof had the same color as the surface. The conidial structures were abundantly observed.

TABLE 1

| (1) Cultural properties of No. 16616 strain | |
|---|---|
| Medium | Cultural properties |
| Malt extract agar* | |
| Growth: | restricted, diameter 1.5–2.0 cm. |
| Surface: | circular, flat, felty, abundant formation of an anamorph, a central portion and a peripheral portion are white to light yellow (5A3), a portion therebetween is olive brown (4F4). |
| Reverse: | a central portion is olive (3F3), a peripheral portion is orange white (5A2). |
| Potato dextrose agar (Difco 0013) | |
| Growth: | restricted, diameter 1.5–2.0 cm. |

TABLE 1-continued

(1) Cultural properties of No. 16616 strain

| Medium | Cultural properties |
|---|---|
| Surface: | circular, felty or cottony, somewhat raised, abundant formation of an anamorph, a central portion and a peripheral portion are white to yellowish white (4A3) a portion therebetween is grayish brown (5F3). |
| Reverse: | a central portion is olive brown (4F3), a peripheral portion is yellowish white (4A2). |
| Czapek's agar* | |
| Growth: | restricted, diameter 2.0–2.5 cm. |
| Surface: | circular, cottony, abundant formation of an anamorph, white. |
| Reverse: | white to yellowish white (3A2). |
| Sabouraud's dextrose agar (Difco 0190) | |
| Growth: | restricted, diameter 1.0–2.0 cm. |
| Surface: | circular, cottony, raised, abundant formation of an anamorph, a central portion is grayish brown (7E3), a peripheral portion is yellowish gray (4B2) to light orange (5A3) forming a light orange soluble pigment. |
| Reverse: | olive brown (4F4) or light orange (5A3). |

TABLE 2

(2) Cultural properties of No. 16616 strain

| Medium | Cultural properties |
|---|---|
| YpSs agar (Difco 0739) | |
| Growth: | restricted, diameter 2.0–2.5 cm. |
| Surface: | circular flat, felty or cottony, abundant formation of an anamorph, white to light orange (4A3). |
| Reverse: | light orange (4A3). |
| Corn meal agar (Difco 0386) | |
| Growth: | restricted, diameter 1.5–2.0 cm. |
| Surface: | circular, flat, thin, felty, abundant formation of an anamorph, a central portion is olive gray (2F3), a peripheral portion is yellowish white (3A2). |
| Reverse: | a central portion is olive grayish brown (2F2), a peripheral portion is yellowish white (3A2). |
| MY20 agar* | |
| Growth: | very restricted, diameter 0.5–1.0 cm. |
| Surface: | circular, raised, felty, abundant formation of an anamorph, white to yellowish gray (4B2). |
| Reverse: | a central portion is yellowish brown (5FA), a peripheral portion is bright orange (5A4). |

In the above-mentioned cultural properties, the compositions of the asterisked malt extract agar, Czapek's agar and MY20 agar were based on the JCM catalogue (Nakase T., 5th ed., p. 503, Japan Collection of Microorganisms and Life Science Research Information Section of the Institute of Physical and Chemical Research, Saitama, 1992).

These properties were observed after incubation at 25° C. for 14 days from the inoculation. The colors were described according to Methuen Handbook of Colour (Kornerup, A. and J. H. Wanscher, 3rd ed., p. 525, Methuen, London, 1978).

The morphological properties were determined on the basis of the incubation on a Miura medium (Miura, K. and Kudo, M., Trans. Mycol. Soc. Japan, 11: 116–118, 1970). The conidiophore is macronematous or semi-macronematous, solitary, colorless to brown and smooth-surfaced; it is directly raised from the surface of the medium or differentiated from an aerial hypha as a short branch. The conidiophore is simple or slightly branched, and forms phialides solitarily or verticillately. The phialide is colorless and smooth-surfaced, and has a flask-like shape consisting of an elliptically swollen base and an elongated cylindrical stem. The base has a size of 5–8(–10)2×–3 $\mu$m, and the stem has a size of 2.5–5(–6)×1–1.5 $\mu$m. Conidia which are produced continuously form a sticky mass, and sometimes form a chain. The conidium is colorless, smooth-surfaced, unicellular and globose or subglobose, and has a size of 3–4×2.5–3 $\mu$m. A vegetative mycelium is smooth-surfaced, septate, and is branched with a color of from dark brown to light brown. The hyphal cell is cylindrical and has a width of from 1.0 to 3.0 $\mu$m. No chlamydospore is observed, but a single phialo-conidium is sometimes formed on the tip of a phialide.

No. 16616 strain can be grown at from 3° to 30° C., and the optimum growth temperature is between 16° and 22° C. These data were determined on a potato dextrose agar (made by Nissui).

The above-mentioned mycological properties were studied. As a result, according to the classification of microorganisms belonging to the genus Tolypocladium (Bissett, J.: Can, J, Bot., 61: 1311–1329, 1983), No. 16616 strain is similar to Tolypocladium parasiticum Barron 1980. This microorganism was first described by Barron as a parasite of a rotifer that lives in a soil on the waterside. However, it can also be grown under pure culture conditions. No. 16616 strain and T. parasiticum are different only with respect to forming of chlamydospore. T. parasiticum formed the chlamydospore both on the culture medium and on the rotifer. Meanwhile, No. 16616 strain only formed a sole phialo-conidium similar to chlamydospore on the tip of a phialide. With respect to the other properties, No. 16616 strain agreed with T. parasiticum. Accordingly, No. 16616 strain was identified as a strain of T. parasiticum. This No. 16616 strain has been deposited at the National Institute of Bioscience and Human-Technology of the Agency of Industrial Science and Technology under Deposit No. FERM BP-5553 (original deposit date: May 25, 1995).

It should be understood that the specific microorganism which is mentioned only for explanation of the production of WF16616 substance described in the present specification is not critical. The present invention includes the use of all of WF16616 substance-productive mutants including synthetic mutants which can be obtained by the mutation of the microorganism described in the present invention through irradiation with X-rays or ultraviolet light or upon use of N-methyl-N'-nitro-N-nitrosoguanidine or 2-aminopurine and natural mutants.

WF16616 substance of the present invention can be produced by cultivation (for example, shaking culture or aeration stirring culture) of a WF16616 substance-productive fungus (for example, No. 16616 strain) belonging to filamentous fungi in a nutrient medium containing carbon and nitrogen sources which can be assimilated by this fungus.

Preferable examples of the carbon source include glucose, sucrose, starch, modified starch, fructose, glycerin and other carbohydrates.

Preferable examples of the nitrogen source include oatmeal, yeast extract, peptone, gluten meal, cottonseed meal, cottonseed oil cake, soybean meal, corn steep liquor, dry yeast, wheat germs, peanut flour and chicken bone and meat meal. Also available are inorganic or organic nitrogen compounds such as ammonium salts (for example, ammonium nitrate, ammonium sulfate ammonium phosphate), urea and amino acids.

These carbon and nitrogen sources are preferably used in combination. However, pure sources are not altogether necessary. Impure sources often contain growth factors or micronutrients, and these are sometimes advantageous.

For example, an inorganic salt may be added to a medium as required. Examples of the inorganic salt include sodium carbonate, potassium carbonate, sodium phosphate, potassium phosphate, sodium chloride, potassium chloride, sodium iodide, potassium iodide, magnesium salts, copper salts and cobalt salts.

Especially, when a medium is strongly foamed, liquid paraffin, animal oil, vegetable oil, mineral oil or silicone may be added thereto as required.

When the desired substance is mass-produced, aeration stirring culture is preferable as in the production of other fermentative substances. When the desired substance is produced in a small amount, shaking culture in a flask is preferable.

When the cultivation is conducted in a large tank, it is preferable, for preventing delaying in the production of WF16616 substance, that a WF16616 substance-productive fungus be first inoculated and incubated in a relatively small amount of a medium and the resulting culture be then moved to a large tank where it is cultivated for the production of the substance. In this case, the compositon of the medium to be used for the precultivation and the composition of the medium to be used for the production cultivation may be the same or different as required.

The cultivation is preferably conducted under aeration stirring conditions. For example, a known method such as stirring with a propeller or other machine, rotation or shaking of a fermenter, treatment with a pump, air blowing or the like is appropriately employed. Sterile air is used for aeration.

The cultivation temperature can appropriately be changed within such a range that WF16616 substance-productive fungi produce WF16616 substance. It is usually between 9° and 39° C., preferably between 23° and 30° C. The cultivation time varies with the cultivation conditions or the cultivation amount. It is usually between approximately 1 day and 2 weeks.

After the completion of the fermentation, the desired WF16616 substance is recovered from the culture broth. That is, from the cultivated fungus (or the cultivated fungus-containing culture broth) the desired substance is extracted directly with water and/or an organic solvent, or the cultivated fungus is milled mechanically or by a known means such as supersonic waves or the like, then the desired substance being extracted with water and/or an organic solvent, and recovered and purified in a usual manner. In the case of the filtered culture broth, it may be directly recovered and purified in a usual manner.

For recovering and purifying, usual methods may be employed which include, for example, extraction with a solvent such as water, an organic solvent or a mixed solvent thereof, chromatography and recrystallization with a single solvent or a mixed solvent. These methods may be adopted singly or in combination.

WF16616 substance is recovered and purified by the above-mentioned known methods. For example, the culture broth is subjected to extraction using acetone, and the obtained extract is further subjected to ion-exchange resin treatment and silica-gel treatment. The thus-obtained substance is purified through chromatography. The purification is further repeated as required, and its dry powder can finally be obtained.

The physico-chemical properties of the thus-obtained WF16616 substance are shown in Tables 3, 4 and 5.

Table 3
(1) Physico-chemical properties of a salt (considered to be a sodium salt, a potassium salt, an ammonium salt or a mixture thereof) of WF16616 substance (1) Color and state of the substance
white powder
(2) Molecular formula
$C_{51}H_{82}N_8O_{21}S$ (as a free acid)
(3) Molecular weight
FAB-MS m/z 1291 (M+2Na-H)
(4) Decomposition point
210°–215° C. (decomp.)
(5) Specific rotation
$[\alpha]_D^{23}$: −20° (c=1.0; methanol)
(6) UV absorption spectrum
$\lambda_{max}^{H_2O}$: 270
$\lambda_{max}^{0.01N\ NaOH}$: 245, 290

Table 4
(2) Physico-chemical properties of WF16616 substance (7) IR absorption spectrum
$\nu_{max}^{KBr}$: 3350, 2959, 2926, 2856, 1670, 1629, 1534, 1442, 1402, 1273, 1148, 1048, 969, 946, 885, 805 cm$^{-1}$
(8) Solubility in a solvent
easily soluble in methanol
sparingly soluble in ethyl acetate and acetone
insoluble in chloroform
(9) Color reaction
positive: ninhydrin reaction, cerium sulfate reaction, iodine steam reaction
negative: ferric chloride reaction, Molish's reaction, Ehrlich's reaction
(10) Classification of an acid substance and a basic substance
acid substance Table 5
(3) Physico-chemical properties of WF16616 substance

(11) $^1$H nuclear magnetic resonance spectrum (500 MHz, CD$_3$OD)
$\delta_H$: 7.31(1H, d, J=2 Hz), 7.02(1H, dd, J=2 and 8 Hz), 6.86(1H, d J=8 Hz), 5.24(1H, d, J=3 Hz), 5.06(1H, d, J=4 Hz), 4.94(1H, d J=3 Hz), 4.59–4.48(3H, m), 4.47–4.34(5H, m), 4.28(1H, dd, J=2 and 6 Hz), 4.16(1H, m), 4.07(1H, m), 3.98–3.89(2H, m), 3.75 (1H, d J=1 Hz), 3.35(1H, t J=10 Hz), 2.76(1H, dd J=4 and 5 Hz), 2.51(1H, m), 2.45(1H, dd, J=8 and 16 Hz), 2.39(1H, dd, J=7 and 16 Hz), 2.21(2H, t, J=7 Hz), 2.03–1.94(3H, m), 1.57(2H, m), 1.50–1.38(2H, m), 1.37–1.20(12H, m), 1.17(3H d, J=6 Hz), 1.12–1.04(3H, m), 1.05(3H, d, J=7 Hz), 0.90(1H, m), 0.87(3H, t, J=7 Hz), 0.85(3H, d, J=6 Hz), 0.84(3H, d, J=6 Hz).
The chart is shown in FIG. 1.
(12) $^{13}$C nuclear magnetic resonance spectrum (125 MHz, CD$_3$OD)
$\delta_c$: 176.9(s), 175.8(s), 174.4(s), 173.5(s), 172.7(s), 172.6(s), 172.5(s), 169.3(s), 150.3(s), 141.1(s), 134.5(s), 125.6(d), 123.2(d), 118.2(d), 76.4(d), 75.7 (d), 75.5(d), 74.2(d), 71.3(d), 70.7(d), 70.6(d), 70.1 (d), 68.2(d), 62.4(d), 58.4(d), 57.1(t, CH$_2$), 56.9(d), 55.5(d), 53.0(t, $CH_2$), 51.4(d), 45.9(t, $CH_2$), 39.6(t, $CH_2$), 39.1(d), 38.4(t, $CH_2$), 38.1(t, $CH_2$), 36.7(t, $CH_2$), 34.9(t, $CH_2$), 32.9(d), 31.2(d), 31.1(t, $CH_2$), 30.7(t, $CH_2$), 30.6(t, $CH_2$), 30.3(t, $CH_2$), 30.3(t, $CH_2$), 28.0(t, $CH_2$), 27.0(t, $CH_2$), 20.7(q), 20.2(q), 19.8(q), 11.6(q), 11.1(q).

Figure 2:
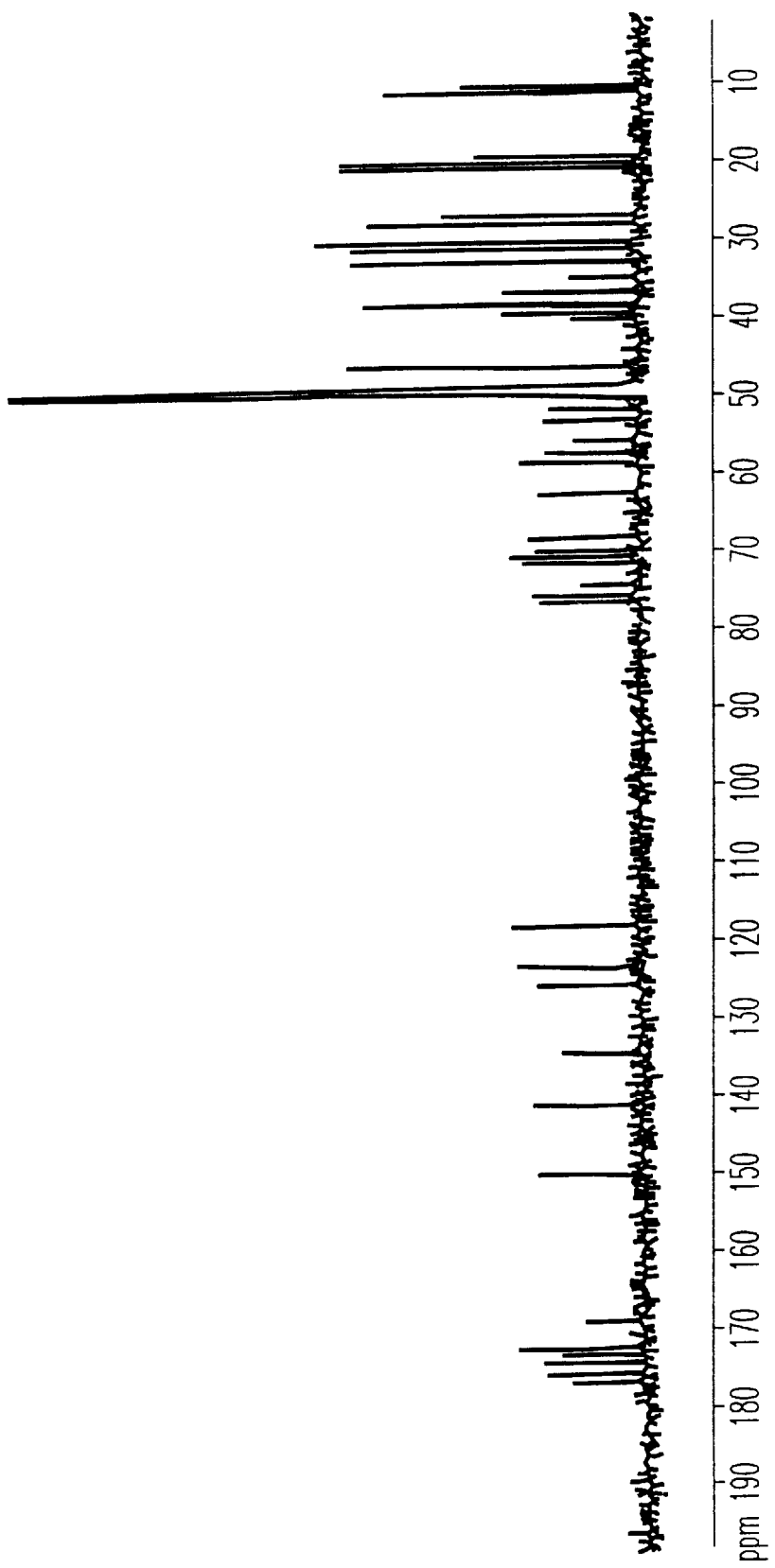
FIG. 2 is a chart showing a $^{13}$C nuclear magnetic resonance spectrum of a salt (which is considered to be a sodium salt, a potassium salt, an ammonium salt or a mixture thereof) of WF16616 substance.

The chart is shown in FIG. 2.

It is identified, as will be described later, that WF16616 substance of the present invention exhibits an excellent physiological activity, especially an excellent antifungal or antiprotozoan activity as well as a low toxicity and a high safety, and is quite effective as an antifungal agent or as an antiprotozoan agent.

Accordingly, the substance of the present invention can be used as an active ingredient of a medication, and such a medication is also included in the present invention. The composition of the medication in the present invention can be formed by adding an ordinary organic or inorganic carrier to WF16616 substance and/or its salt as an active ingredient. This composition is formulated into a solid, semi-solid or liquid oral administration agent or parenteral administration agent for external use, etc.

The oral administration agent may take the form of tablets, pills, granules, soft or hard capsules, powders, fine granules, grains, emulsions, suspensions, syrups, pellets or elixirs. The parenteral administration agent may take the form of injections, drops, infusions, ointments, lotions, tonics, sprays, suspensions, oil solutions, emulsions and suppositories. The acitve ingredient of the present invention may be formulated into preparations in a usual manner. At this time, ordinary adjuvant may be appropriately used as required. Examples of the adjuvant include surfactants, excipients, coloring agents, flavors, preservatives, stabilizers, buffers, suspending agents and isotonic agents.

The dose of the composition in the present invention varies depending on the type of the composition, the type of the disease to be prevented or treated, the administration method, the age of the patient, the degree of progression of the disease, the treatment time and the like. In the case of intravenous administraiton, the dose of the active ingredient (WF16616 substance or/and its salt) is between 0.01 and 1,000 mg/kg, preferably between 0.1 and 100 mg/kg per day for an adult. In the case of intramuscular administration, it is between 0.01 and 1,000 mg/kg, preferably between 0.1 and 100 mg/kg per day for an adult. In the case of oral administration, it is between 0.5 and 2,000 mg/kg, preferably between 1 and 1,000 mg/kg per day for an adult.

The present invention is illustrated more specifically by referring to the following Examples.

EXAMPLE 1

Fermentative Production of WF16616 Substance (1) Incubation

An aqueous seed medium containing glycerol (2%), sucrose (2%), cottonseed meal (2%), dry yeast (1%), polypeptone (1%), $KH_2PO_4$ (0.1%) and Tween 80 (0.1%) was added to each of three 500-ml Erlenmeyer flasks in an amount of 160 ml each, and was sterilized at 120° C. for 30 minutes. One loopful of a slant culture of No. 16616 strain which had been fully grown upon incubation in a YpSs agar medium at 25° C. for 2 weeks was inoculated in the above-mentioned sterilized medium, and was incubated at 25° C. for 1 week while being shaken using a rotary shaker at 220 rpm and a stroke of 5.1 cm.

An aqueous productive medium containing corn starch (2%), glucose (1%), cotton seed meal (1%), soybean meal (0.5%) and dry yeast (0.5%) was charged into a 30-liter stainless steel jar fermenter, and was sterilized at 120° C. for 30 minutes.

The above-obtained seed culture was inoculated in 20 liters of the sterilized productive medium, and the fermentation was continued at 25° C. for 6 days while being stirred at 200 rpm upon aeration at a rate of 20 liters/min.

(2) Separation and Purification

After the completion of the incubation, to 15 liters of the culture broth, is added the same amount of acetone, and the mixture was subjected to extraction at room temperature for 2 hours. To the resulting mixture, was added a diatomaceous earth for filtration. The obtained filtrate was concentrated by removing acetone under reduced pressure. The pH of the concentrate was adjusted to 3.95 with conc. $H_2SO_4$, and the concentrate was then subjected to adsorption treatment using 0.75 liters of a high-molecular adsorbent Diaion HP-20 (made by Mitsubishi Kagaku Co.). The column was washed with water and with 50% aqueous methanol, and elution was then carried out with methanol and with acetone.

The eluate (3.75 liters) was evaporated to dryness under reduced pressure. The thus-obtained dry substnace was dissolved in a small amount of methanol, and 100 ml of silica gel (Kiesel gel 60, made by E. Merck Co.) was added thereto to form a slurry. Methanol was removed, and the residual dry powder was applied to a column (200 ml) of the above-mentioned silica gel. The column was developed with ethyl acetate, with acetone and with a mixed solution of acetone and methanol. Two-hundred milliliters of the active fraction which was eluted with the mixed solution of acetone and methanol (at a ratio of 10:1 and 1:1) was concentrated to dryness under reduced pressure.

The resulting residue was dissolved in 200 ml of 50% aqueous methanol, and was subjected to YMC-gel (ODS-AM, 120-S50, made by YMC, 350 ml) chromatography. The column was washed with 50% aqueous methanol and with 60% aqueous methanol, and elution was carried out with 70% aqueous methanol. Fractions containing the active substance were mixed together to come to 500 ml, and the 500 ml was concentrated under reduced pressure to obtain 160 ml of the resulting aqueous methanol solution.

This solution was subjected to preparative HPLC, YMC column (ODS-AM, SH-343-5AM, S-5, 250×20 mm i.d.) chromatography, and was eluted at a flow rate of 16 ml/min using 45% aqueous acetonitrile containing $NH_4H_2PO_4$ (0.5%). One hundred milliliters of the active fraction was collected, and diluted to twice with water. This solution was applied to a YMC column (ODS-AM, SH-343-5AM, S-5, 250×20 mm i.d.). The column was washed with 50% aqueous methanol, and was then developed at the above-mentioned flow rate using 60% aqueous methanol. One hundred milliliters of the eluate was concentrated under reduced pressure, and was then freeze-dried to obtain 46.6 mg of a white powder which is the salt of WF16616 substance (considered to be a sodium salt, a potassium salt, an ammonium salt or a mixture thereof).

EXAMPLE 2

Biological Properties of WF16616 Substance (1) Antifungal Activity

The antifungal activity of WF16616 substnace was measured in a 0.5% glucose-containing yeast nitrogen base (YNBD) medium by a microbroth dilution analysis method using a 96-well microtiter plate. This substance was dissolved in methanol, and was diluted to twice in sequence in the microtiter plate using the YNBD medium.

The test microorganism was inoculated at a concentration of $1\times10^4$ cfu/100 $\mu$l/well. Candida albicans and Aspergillus fumigatus were incubated in the above-mentioned plate at 37° C. for 22 hours, and Cryptococcus neoformans at 30° C. for 48 hours, respectively. Then, MIC was measured through microscopical observation. The results are shown in Table 6. As is clear from the results, it was identified that the substance of the present invention exhibited the outstanding antifungal activity.

TABLE 6

|  | MIC (μg/ml) |
|---|---|
| Candida albicans No. 7 | 0.78 |
| Candida albicans FP633 | 0.10 |
| Aspergillus fumigatus FD050 | 0.16 |
| Cryptococcus neoformans YC203 | >50 |

(2) Toxicity Test

WF16616 substance was intraperitoneally injected into each of five 5-week-old ICR female mice at a dose of 5 mg/kg once a day for three days. However, none of the mice were dead, and the increase in the weight of these mice was quite the same as that in the weight of unadministered mice. It was thus identified that WF16616 substance exhibited a high safety.

EXAMPLE 3
Production of an Injection

| (1) | WF16616 substance produced in Example 1 | 5 g |
| (2) | NaCl | 9 g |
| (3) | sodium hydrogencarbonate | 1 g |

All of the above-mentioned ingredients (1) to (3) were dissolved in 100 ml of distilled water, and 1 ml of the resulting solution was charged into an ampoule. Thus, 100 ampoules of the injection were prepared.

Effects of the Invention

The present invention is to provide WF16616 substance. This substance is a novel substance which exhibits an excellent physiological activity and which can be used for various medications as antimicrobial agents, especially, e.g., as an antifungal agent and as an agent for Pneumocystis carinii pneumonia.

Statement on the Microorganism Deposited Under Regulation No. 13-2
1. Tolypocladium parasiticum No. 16616
   a. Name and address of a depository in which the above-mentioned microorganism was deposited: Name: National Institute of Bioscience and Human-Technology of the Agency of Industrial Science and Technology, Ministry of International Trade and Industry Address: 1–3, Higashi 1 chome, Tsukuba-shi, Ibaraki-ken, 305 Japan
   b. Date on which the microorganism was deposited in the depository described in a: May 25, 1995
   c. Deposit No. which was allotted by the depository described in a: FERM BP-5553

Additional Explanation on the Deposit of the Microorganism

The above-mentioned deposit, FERM BP-5553, is the deposit transferred on May 30, 1996 from the National deposit No. FERM P-14941 deposited on May 25, 1995 (the original deposit date.

We claim:

1. WF16616 substance represented by the following structural formula (1) or its pharmaceutically acceptable salt.

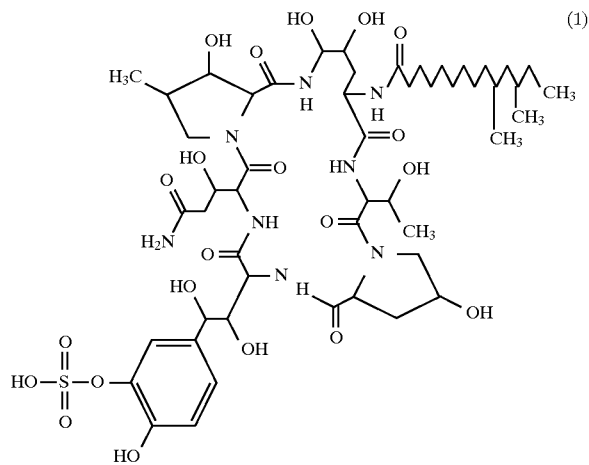

2. A process for producing WF16616 substance, which comprises culturing a WF16616 substance-productive fungus belonging to the genus Tolypocladium to produce WF16616 substance, and isolating this substance.

3. The process of claim 2, wherein the WF16616 substance-productive fungus is Tolypocladium parasiticum.

4. A pharmaceutical preparation comprising WF16616 substance or its pharmaceutically acceptable salt, and a pharmaceutically acceptable, substantially non-toxic carrier or excipient.

5. The pharmaceutical preparation of claim 4 which is used as an antifungal agent.

* * * * *